US012715845B2

(12) United States Patent
Haydl et al.

(10) Patent No.: US 12,715,845 B2
(45) Date of Patent: Aug. 25, 2026

(54) PROCESS FOR PREPARING N,N'-BIS(2,2,6,6-TETRAMETHYLPIPERIDIN-4-YL) HEXANE-1,6-DIAMINE

(71) Applicant: BASF SE, Ludwigshafen am Rhein (DE)

(72) Inventors: Alexander Michael Haydl, Mannheim (DE); Michael Schmitt, Ludwigshafen am Rhein (DE); Elena Capito', Pontecchio Marconi (IT)

(73) Assignee: BASF SE, Ludwigshafen am Rhein (DE)

( * ) Notice: Subject to any disclaimer, the term of this patent is extended or adjusted under 35 U.S.C. 154(b) by 306 days.

(21) Appl. No.: 18/279,567

(22) PCT Filed: Feb. 10, 2022

(86) PCT No.: PCT/EP2022/053192

§ 371 (c)(1),
(2) Date: Aug. 30, 2023

(87) PCT Pub. No.: WO2022/184399

PCT Pub. Date: Sep. 9, 2022

(65) Prior Publication Data

US 2024/0182417 A1 Jun. 6, 2024

(30) Foreign Application Priority Data

Mar. 5, 2021 (EP) .................................... 21161133

(51) Int. Cl.
*C07D 211/02* (2006.01)
*C07D 251/22* (2006.01)

(52) U.S. Cl.
CPC .......... *C07D 211/02* (2013.01); *C07D 251/22* (2013.01)

(58) Field of Classification Search
CPC .... C07D 211/02; C07D 251/22; C07D 211/58
USPC .......................................................... 544/180
See application file for complete search history.

(56) References Cited

U.S. PATENT DOCUMENTS

| | | | |
|---|---|---|---|
| 4,086,204 | A | 4/1978 | Cassandrini et al. |
| 5,945,536 | A | 8/1999 | Jegelka et al. |
| 6,011,157 | A | 1/2000 | Julius et al. |
| 6,407,254 | B1 | 6/2002 | Riva et al. |
| 2003/0146542 | A1 | 8/2003 | Fatnes et al. |
| 2010/0160637 | A1 | 6/2010 | Haremza et al. |

FOREIGN PATENT DOCUMENTS

| | | | |
|---|---|---|---|
| CA | 2060546 | C | 7/2002 |
| CN | 1336365 | A | 2/2002 |
| CN | 107033127 | A | 8/2017 |
| CN | 107488141 | A | 12/2017 |
| CN | 108623566 | A | 10/2018 |
| DE | 19622269 | A1 | 12/1997 |
| EP | 0508940 | A1 | 10/1992 |
| EP | 0782994 | A1 | 7/1997 |
| EP | 0857719 | A1 | 8/1998 |
| EP | 0906281 | A1 | 4/1999 |
| EP | 0906281 | B1 | 11/2001 |
| WO | 0162833 | A1 | 8/2001 |
| WO | 2008145673 | A2 | 12/2008 |

OTHER PUBLICATIONS

International Search Report mailed May 17, 2022 in PCT/EP2022/053192.

*Primary Examiner* — Taylor V Oh
(74) *Attorney, Agent, or Firm* — ArentFox Schiff LLP

(57) ABSTRACT

The present invention relates to a process for preparing N,N'-bis(2,2,6,6-tetramethylpiperidin-4-yl)hexane-1,6-diamine. The present invention further relates to the use of N,N'-bis(2,2,6,6-tetramethylpiperidin-4-yl)hexane-1,6-diamine to prepare poly[[6-[(1,1,3,3-tetramethylbutyl)amino]-s-triazine-2,4-diyl]-[(2,2,6,6-tetramethyl-4-piperidyl) imino]-hexamethylene-[(2,2,6,6-tetramethyl-4-piperidyl) imino], reaction material of 1,6-hexanediamine, N,N'-bis (2,2,6,6-tetramethyl-4-piperidine-yl),2,4,6-trichloro-1, 3,5-triazine,N-butyl-1-butylamine, and N-butyl-2,2,6,6-tetramethyl-4-piperidineamine, N,N'-bis(2,2,6,6-tetramethyl-4-piperidyl)-N,N'-diformylhexamethylenediamine, and 1,6-Hexanediamine, N,N'-bis(2,2,6,6-tetramethyl-4-piperidinyl)-, polymer with 2,4-dichloro-6-(4-morpholinyl)-1,3,5-triazine.

16 Claims, No Drawings

PROCESS FOR PREPARING N,N'-BIS(2,2,6,6-TETRAMETHYLPIPERIDIN-4-YL) HEXANE-1,6-DIAMINE

CROSS-REFERENCE TO RELATED APPLICATIONS

This application is a National Stage Entry of PCT/EP2022/053192, filed Feb. 10, 2022, which claims priority to European Patent Application No. 21161133.0, filed Mar. 5, 2021, the disclosures of each of which are hereby incorporated by reference in their entirety.

FIELD OF THE INVENTION

The present invention relates to a process for preparing N,N'-bis(2,2,6,6-tetramethylpiperidin-4-yl)hexane-1,6-diamine. The present invention further relates to the use of N,N'-bis(2,2,6,6-tetramethylpiperidin-4-yl)hexane-1,6-diamine to prepare poly[[6-[(1,1,3,3-tetramethylbutyl)amino]-s-triazine-2,4-diyl]-[(2,2,6,6-tetramethyl-4-piperidyl) imino]-hexamethylene-[(2,2,6,6-tetramethyl-4-piperidyl) imino], reaction material of 1,6-hexanediamine, N,N'-bis (2,2,6,6-tetramethyl-4-piperidine-yl),2,4,6-trichloro-1, 3,5-triazine,N-butyl-1-butylamine, and N-butyl-2,2,6,6-tetramethyl-4-piperidineamine, N,N'-bis(2,2,6,6-tetramethyl-4-piperidyl)-N,N'-diformylhexamethylenediamine, and 1,6-Hexanediamine, N,N'-bis(2,2,6,6-tetramethyl-4-piperidinyl)-, polymer with 2,4-dichloro-6-(4-morpholinyl)-1,3,5-triazine.

BACKGROUND OF THE INVENTION

Synthesis of amines on an industrial scale comprising an imination reaction, followed by subsequent hydrogenation is well known and has been described in the past for the synthesis of 4-amino piperidines either by batch or later by continuous process. Both technologies prelude by an imine formation, catalyzed by water or by Lewis and/or Bronsted acids and followed by transition metal catalyzed reductive amination using pressurized hydrogen to give N,N'-bis(2,2,6,6-tetramethylpiperidin-4-yl)hexane-1,6-diamine as crude compound (94-97%) which is then purified by distillation under reduced pressure or used without further purification.

EP0508940 discloses the batch catalysis which is carried out in 4 hours at 90 C as one single batch cycle using Pt/C at high pressure of hydrogen (50 bar). This is done to circumvent a purification process of distillation leading to a lower yield. The major drawbacks within this described process are the requirement of rather elevated hydrogen pressure (50 bar), the need for specific equipment and subsequently extra safety measures, use of an excess of hydrogen which is vented into the waste-air stream, lower catalyst lifetime by limitations in the number of cycles (typically only maximum 10-20 cycles per batch catalyst) and primarily the color instability of the obtained N,N'-bis (2,2,6,6-tetramethylpiperidin-4-yl)hexane-1,6-diamine (in terms of leading to high APHA values under thermal stress, e.g. at 60° C.) and the drawbacks with the color itself (due to absence of a distillation), which hampers the transmittance (T %) value of the products downstream the value chain leading to lower quality of the product.

The continuously operated N,N'-bis(2,2,6,6-tetramethylpiperidin-4-yl)hexane-1,6-diamine process has also been previously reported in EP0857719 and U.S. Pat. No. 5,945,536 as one-pot imination/hydrogenation process proceeding at very high hydrogen pressures (285 bars), elevated temperatures (90-190° C.) by fixed bed catalysts (transition-metal catalysis, e.g. [Pd], [Pt] or [Co] on a solid support, e.g. $Al_2O_3$ or $SiO_2$) in a tube reactor. Although high selectivity of up to 94% N,N'-bis(2,2,6,6-tetramethylpiperidin-4-yl) hexane-1,6-diamine is achieved with this process, compared to the N,N'-bis(2,2,6,6-tetramethylpiperidin-4-yl)hexane-1,6-diamine obtained by batch reaction in which the residues (after removing the light-boilers) can directly be used to prepare the products downstream the value chain, the crude material obtained by the reported continuous setup requires an extra purification step at harsh distillation conditions (b.p. 225° C. at 6 mbar in which the HMBTAD is obtained with APHA values between 90-190 after distillation) because of a lack in color of the crude material (APHA value of 703).

To increase the quality of distilled 4-aminopiperidines, specifically its color quality to secure a long-term stability, procedures for the treatment of distilled 4-aminopiperidines with additives (e.g. with $NaBH_4$ in EP0906281 and DE19622269) are known. However, this treatment suffers from the drawbacks that an extra step relying on a separate reactor setup is required, in addition to the needs of prior distilled material for this purification concept.

Thus, an object of the present invention is to provide a process for the preparation of N,N'-bis(2,2,6,6-tetramethylpiperidin-4-yl)hexane-1,6-diamine in high selectivity. Another object of the present invention is to provide a simple and economic process for preparation of N,N'-bis(2,2,6,6-tetramethylpiperidin-4-yl)hexane-1,6-diamine.

Still another objection of the present invention is to provide a process for preparing stable N,N'-bis(2,2,6,6-tetramethylpiperidin-4-yl)hexane-1,6-diamine.

SUMMARY OF THE INVENTION

Surprisingly, it was found that by combining the batch hydrogenation process with a continuous post hydrogenation process, N,N'-bis(2,2,6,6-tetramethylpiperidin-4-yl) hexane-1,6-diamine is obtained in a higher selectivity. Further, combination of the batch hydrogenation with a continuous post hydrogenation provides technically and economically feasible process conditions by refraining from any purification step to produce stable N,N'-bis(2,2,6,6-tetramethylpiperidin-4-yl)hexane-1,6-diamine with improved transmittance (T %) values of its downstream products.

Transmittance (T %) is related to optical depth and to absorbance as T=e^(−T)=10^(−A), where T is the optical depth; A is the absorbance.

Thus, in an aspect, the presently claimed invention is directed to a process for preparing N,N'-bis(2,2,6,6-tetramethylpiperidin-4-yl)hexane-1,6-diamine, wherein the process comprises:

i. iminating 2,2,6,6-tetramethylpiperidin-4-one with 1,6-hexamethylenediamine to obtain a first mixture comprising N,N'-(hexane-1,6-diyl)bis(2,2,6,6-tetramethylpiperidin-4-imine);

ii. hydrogenating N,N'-(hexane-1,6-diyl)bis(2,2,6,6-tetramethylpiperidin-4-imine) of the first mixture to obtain a hydrogenated second mixture comprising 50 to 99.5 wt % of N,N'-bis(2,2,6,6-tetramethylpiperidin-4-yl)hexane-1,6-diamine; and iii. continuous hydrogenating of the second mixture in a fixed bed reactor to obtain N,N'-bis(2,2,6,6-tetramethylpiperidin-4-yl)hexane-1,6-diamine.

In another aspect, the presently claimed invention is directed to the use of N,N'-bis(2,2,6,6-tetramethylpiperidin-4-yl)hexane-1,6-diamine, obtained by the process discussed hereinabove, to prepare poly[[6-[(1,1,3,3-tetramethylbutyl)

amino]-s-triazine-2,4-diyl]-[(2,2,6,6-tetramethyl-4-piperidyl)imino]-hexamethylene-[(2,2,6,6-tetramethyl-4-piperidyl)imino], reaction material of 1,6-hexanediamine, N,N'-bis (2,2,6,6-tetramethyl-4-piperidine-yl),2,4,6-trichloro-1,3,5-triazine,N-butyl-1-butylamine, and N-butyl-2,2,6,6-tetramethyl-4-piperidineamine, N,N'-bis(2,2,6,6-tetramethyl-4-piperidyl)-N,N'-diformylhexamethylenediamine, and 1,6-Hexanediamine, N,N'-bis(2,2,6,6-tetramethyl-4-piperidinyl)-, polymer with 2,4-dichloro-6-(4-morpholinyl)-1,3,5-triazine.

DETAILED DESCRIPTION OF THE INVENTION

Before the present compositions and formulations of the invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims. If hereinafter a group is defined to comprise at least a certain number of embodiments, this is meant to also encompass a group which preferably consists of these embodiments only. Furthermore, the terms “first”, “second”, “third” or “(a)”, “(b)”, “(c)”, “(d)” etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms “first”, “second”, “third” or “(A)”, “(B)” and “(C)” or “(a)”, “(b)”, “(c)”, “(d)”, “i”, “ii” etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to “one embodiment” or “a preferred embodiment” means that a particular feature, structure or characteristic described in connection with the embodiment is included in at least one embodiment of the presently claimed invention. Thus, appearances of the phrases “in one embodiment” or “in a preferred embodiment” or “in another embodiment” in various places throughout this specification are not necessarily all referring to the same embodiment but may. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the invention, and form different embodiments, as would be understood by those in the art. For example, in the appended claims, any of the claimed embodiments can be used in any combination.

Furthermore, the ranges defined throughout the specification include the end values as well i.e. a range of 1 to 10 implies that both 1 and 10 are included in the range. For the avoidance of doubt, the applicant shall be entitled to any equivalents according to the applicable law.

Certain terms are first defined so that this disclosure can be more readily understood. Unless defined otherwise, all technical and scientific terms used herein have the same meaning as commonly understood by one of ordinary skill in the art to which embodiments of the invention pertain.

In an aspect, the presently claimed invention is related to a process for preparing N,N'-bis(2,2,6,6-tetramethylpiperidin-4-yl)hexane-1,6-diamine, wherein the process comprising:

i. iminating 2,2,6,6-tetramethylpiperidin-4-one with 1,6-hexamethylenediamine to obtain a first mixture comprising N,N'-(hexane-1,6-diyl)bis(2,2,6,6-tetramethylpiperidin-4-imine);

ii. hydrogenating N,N'-(hexane-1,6-diyl)bis(2,2,6,6-tetramethylpiperidin-4-imine) of the first mixture to obtain a hydrogenated second mixture comprising 50 to 99.5 wt % of N,N'-bis(2,2,6,6-tetramethylpiperidin-4-yl)hexane-1,6-diamine; and iii. continuous hydrogenating of the second mixture in a fixed bed reactor to obtain N,N'-bis(2,2,6,6-tetramethylpiperidin-4-yl)hexane-1,6-diamine.

In an embodiment, the presently claimed invention is related to a process for preparing N,N'-bis(2,2,6,6-tetramethylpiperidin-4-yl)hexane-1,6-diamine, wherein the process comprising:

i. iminating 2,2,6,6-tetramethylpiperidin-4-one with 1,6-hexamethylenediamine to obtain a first mixture comprising N,N'-(hexane-1,6-diyl)bis(2,2,6,6-tetramethylpiperidin-4-imine);

ia. dewatering a first mixture to obtain a water-free first mixture comprising N,N'-(hexane-1,6-diyl)bis(2,2,6,6-tetramethylpiperidin-4-imine);

ii. hydrogenating N,N'-(hexane-1,6-diyl)bis(2,2,6,6-tetramethylpiperidin-4-imine) of the first mixture to obtain a hydrogenated second mixture comprising 50 to 99.5 wt % of N,N'-bis(2,2,6,6-tetramethylpiperidin-4-yl)hexane-1,6-diamine; and iii. continuous hydrogenating of the second mixture in a fixed bed reactor to obtain N,N'-bis(2,2,6,6-tetramethylpiperidin-4-yl)hexane-1,6-diamine.

In an embodiment, the presently claimed invention is related to a process for preparing N,N'-bis(2,2,6,6-tetramethylpiperidin-4-yl)hexane-1,6-diamine, wherein the process comprising:

i. iminating 2,2,6,6-tetramethylpiperidin-4-one with 1,6-hexamethylenediamine to obtain a first mixture comprising N,N'-(hexane-1,6-diyl)bis(2,2,6,6-tetramethylpiperidin-4-imine);

ii. hydrogenating N,N'-(hexane-1,6-diyl)bis(2,2,6,6-tetramethylpiperidin-4-imine) of the first mixture to obtain a hydrogenated second mixture comprising 50 to 99.5 wt % of N,N'-bis(2,2,6,6-tetramethylpiperidin-4-yl)hexane-1,6-diamine;

iia. dewatering the second mixture to obtain a water-free second mixture comprising N,N'-(hexane-1,6-diyl)bis(2,2,6,6-tetramethylpiperidin-4-imine); and iii. continuous hydrogenating of the second mixture in a fixed bed reactor to obtain N,N'-bis(2,2,6,6-tetramethylpiperidin-4-yl)hexane-1,6-diamine.

In an embodiment, the presently claimed invention is related to a process for preparing N,N'-bis(2,2,6,6-tetramethylpiperidin-4-yl)hexane-1,6-diamine, wherein the process comprising:

i. iminating 2,2,6,6-tetramethylpiperidin-4-one with 1,6-hexamethylenediamine to obtain a first mixture comprising N,N'-(hexane-1,6-diyl)bis(2,2,6,6-tetramethylpiperidin-4-imine);

ia. dewatering a first mixture to obtain a water-free first mixture comprising N,N'-(hexane-1,6-diyl)bis(2,2,6,6-tetramethylpiperidin-4-imine);

ii. hydrogenating N,N'-(hexane-1,6-diyl)bis(2,2,6,6-tetramethylpiperidin-4-imine) of the first mixture to obtain a hydrogenated second mixture comprising 50 to 99.5 wt % of N,N'-bis(2,2,6,6-tetramethylpiperidin-4-yl)hexane-1,6-diamine;

iia. dewatering the second mixture to obtain a water-free second mixture comprising N,N'-(hexane-1,6-diyl)bis(2,2,6,6-tetramethylpiperidin-4-imine); and iii. continuous hydrogenating of the second mixture in a fixed bed reactor to obtain N,N'-bis(2,2,6,6-tetramethylpiperidin-4-yl)hexane-1,6-diamine.

The process for preparing N,N'-bis(2,2,6,6-tetramethylpiperidin-4-yl)hexane-1,6-diamine is discussed in detail herein below.

Step (i): 2,2,6,6-tetramethylpiperidin-4-one is Iminated with 1,6-hexamethylenediamine to Obtain a First Mixture Comprising N,N'-(hexane-1,6-diyl)bis(2,2,6,6-tetramethylpiperidin-4-imine)

In an embodiment, the molar ratio of 1,6-hexamethylenediamine to 2,2,6,6-tetramethylpiperidin-4-one is in the range of 0.1:5 to 5:0.1, preferably 1:5 to 5:1, more preferably 1:2 to 2:1, and most preferably 1:1.98.

In an embodiment, a temperature of the step (i) is in the range of 60° C. to 200° C., preferably 80° C. to 180° C.

In an embodiment, the first mixture prepared in the step (i) comprises water content in the range of 3 to 7 wt %.

Step (ia): The First Mixture is Dewatered to Obtain a Water-Free First Mixture Comprising N,N'-(hexane-1,6-diyl)bis(2,2,6,6-tetramethylpiperidin-4-imine)

By the term 'water-free' it is meant that the amount of water is less than 2 wt %, based on the total weight of the first mixture.

In an embodiment, water is removed from the first mixture at a pressure in the range of 30 mbar to 60 mbar, preferably 40 mbar to 50 mbar.

In an embodiment, water is removed from the first mixture to have water content less than 2 wt %, preferably 1 wt %.

Step (ii): N,N'-(hexane-1,6-diyl)bis(2,2,6,6-tetramethylpiperidin-4-imine) of the First Mixture is Hydrogenated to Obtain a Hydrogenated Second Mixture Comprising 50 to 99.5 wt % of N,N'-bis(2,2,6,6-tetramethylpiperidin-4-yl)hexane-1,6-diamine In an embodiment, the hydrogenation in the step (ii) is performed using batch technology. For batch technology, batch-type reactors such as isothermally heated and stirred pressure autoclave reactors are used.

In an embodiment, in the step (ii) the second mixture comprises 65 to 95 wt % of N,N'-bis(2,2,6,6-tetramethylpiperidin-4-yl)hexane-1,6-diamine.

In an embodiment, the hydrogenation in the step (ii) is catalyzed using at least one first transition metal.

In an embodiment, the first transition metal is selected from copper, nickel, cobalt, ruthenium, platinum, and palladium, preferably platinum.

The at least one first transition metal catalyst is placed on the solid support of aluminium oxide ($Al_2O_3$), titanium dioxide ($TiO_2$), zirconium dioxide ($ZrO_2$), silicon dioxide ($SiO_2$), and carbon.

The first transition metal catalyst on the solid support is present in an amount in the range of 0.1 to 1.0 wt. % of the total weight of the solid support, preferably 0.7 wt. % of the total weight of the solid support.

Further, the hydrogenation in the step (ii) can be catalyzed using at least one first transition metal without the solid support.

In an embodiment, the pressure of hydrogen in the hydrogenation step (ii) is in the range of 1 to 200 bar, preferably 5 to 100 bar, and more preferably 5 to 35 bar.

In an embodiment, the hydrogenation in the step (ii) is carried out at a temperature in the range of 60° C. to 200° C., preferably in the range of 80° C. to 180° C.

In an embodiment, the step (ii) of hydrogenation is carried out for a time period of 1 hour to 6 hours.

Step (iia): The Second Mixture is Dewatered to Obtain a Water-Free Second Mixture Comprising N,N'-(hexane-1,6-diyl)bis(2,2,6,6-tetramethylpiperidin-4-imine)

The term 'water-free' herein implies a water content of less than 2 wt. %, based on the total weight of the second mixture.

Water is removed from the second mixture by the process of distillation and light boilers at a temperature in the range of 60° C. to 80° C., preferably 60° C. to 70° C., and at a pressure in the range of 100 mbar to 12 mbar.

The mass of 3 to 20 wt % of the starting material is removed containing water, acetone, and traces of 2,2,6,6-tetramethylpiperidin-4-one.

The step (ia) and step (iia) of the water removal from the first mixture and the second mixture, respectively are optional.

Step (iii): The Second Mixture is Continuously Hydrogenated in a Fixed Bed Reactor to Obtain N,N'-bis(2,2,6,6-tetramethylpiperidin-4-yl)hexane-1,6-diamine The step of continuous hydrogenation is performed using adiabatic tubular reactors with a pre-heater or iso-thermic tubular reactors equipped with an inner thermowell both filled with a fixed bed catalyst on a solid support.

In an embodiment, the second mixture comprises water when the step (ia) or the step (iia) are circumvented.

In another embodiment, the second mixture is free of water if water is removed using the step (ia) or the step (iia). The term 'free of water' implies less than 2 Wt. % of water, preferably 0.5 Wt. % of water.

In an embodiment, the continuous hydrogenation of the step (iii) is catalyzed using at least one second transition metal.

In an embodiment, the at least one second transition metal is selected from copper, nickel, cobalt, ruthenium, platinum, and palladium, preferably palladium.

The at least one second transition metal catalyst is placed on the solid support of aluminium oxide ($Al_2O_3$), titanium dioxide ($TiO_2$), zirconium dioxide ($ZrO_2$), silicon dioxide ($SiO_2$), and carbon.

The second transition metal catalyst on the solid support is present in an amount in the range of 0.1 to 1.0 wt. % of the total weight of the solid support, preferably 0.7 wt. % of the total weight of the solid support.

Further, the hydrogenation in the step (ii) can be catalyzed using at least one second transition metal without the solid support.

In an embodiment, the pressure of hydrogen in the hydrogenation step (iii) is in the range of 1 to 200 bar, preferably 5 to 100 bar, and more preferably 5 to 35 bar.

In an embodiment, the temperature of the step (iii) is in the range of 60° C. to 200° C., preferably 80° C. to 180° C., and more preferably 100° C. to 150° C.

In an embodiment, the molar ratio of hydrogen to N,N'-bis(2,2,6,6-tetramethylpiperidin-4-yl)hexane-1,6-diamine in step (iii) is in the range of 0.5:0.1 to 40:5, preferably 1:1 to 40:1, and more preferably 1.5:1 to 35:1.

In an embodiment, the second mixture is fed into the reactor with liquid hour space velocity (LHSV) in the range of 0.5 to 2.0 $kg_{Feed}/L_{cat}$*h, preferably 0.5 to 1.6 $kg_{Feed}/L_{cat}$*h. LHSV is the liquid hourly space velocity, which is the ratio of liquid volume flow per hour to catalyst volume.

In an embodiment, N,N'-bis(2,2,6,6-tetramethylpiperidin-4-yl)hexane-1,6-diamine obtained in step (iii) has APHA value in the range of 90 to 400.

This APHA value serves to quantify the appearance of trace amounts of yellowness, a visual indicator of product degradation due to exposure to light or heat, the presence of impurities and negative effects of processing.

APHA value is determined by using international standard method DIN-ISO 6271 in a colorimeter (Hach Lange type LICO 620) using a round cuvette with 1.2 cm diameter and 8.2 cm height. The molten material (5 mL) was filled into the cuvette and the APHA values were measured hereof.

The post hydrogenation process works with both aqueous and water-free feed resulting from the disrupted batch hydrogenation.

Disrupted batch hydrogenation is an incomplete hydrogenation reaction where the hydrogenation time is reduced by 50% of the time needed for complete conversion to HMBTAD. Typically, it is disrupted at a point when the hydrogenation process slows down and before it reaches the final hydrogen pressure.

In another aspect, the presently claimed invention is directed to the use of N,N'-bis(2,2,6,6-tetramethylpiperidin-4-yl)hexane-1,6-diamine obtained by the process mentioned hereinabove, to prepare poly[[6-[(1,1,3,3-tetramethylbutyl) amino]-s-triazine-2,4-diyl]-[(2,2,6,6-tetramethyl-4-piperidyl)imino]-hexamethylene-[(2,2,6,6-tetramethyl-4-piperidyl)imino], reaction material of 1,6-hexanediamine, N,N'-bis (2,2,6,6-tetramethyl-4-piperidine-yl),2,4,6-trichloro-1,3,5-triazine,N-butyl-1-butylamine, and N-butyl-2,2,6,6-tetramethyl-4-piperidineamine, N,N'-bis(2,2,6,6-tetramethyl-4-piperidyl)-N,N'-diformylhexamethylenediamine, and 1,6-Hexanediamine, N,N'-bis(2,2,6,6-tetramethyl-4-piperidinyl)-, polymer with 2,4-dichloro-6-(4-morpholinyl)-1,3,5-triazine.

The presently claimed invention offers one or more of following advantages:

1. The batch hydrogenation with a continuous post hydrogenation yield N,N'-bis(2,2,6,6-tetramethylpiperidin-4-yl)hexane-1,6-diamine in high selectivity of up to 94%.
2. The post hydrogenation works with both aqueous and water-free feed resulting from the disrupted batch hydrogenation, wherein the conversion is at 65 to 99.5%.
3. Further, combination of the batch hydrogenation with a continuous post hydrogenation allows for technically and economically feasible process conditions by refraining from any purification step (e.g. distillation) to produce stable N,N'-bis(2,2,6,6-tetramethylpiperidin-4-yl)hexane-1,6-diamine with improved transmittance (T %) values of its downstream products.
4. Furthermore, the manufacturing process for N,N'-bis(2,2,6,6-tetramethylpiperidin-4-yl)hexane-1,6-diamine is much more feasible compared to the conventional synthesis of N,N'-bis(2,2,6,6-tetramethylpiperidin-4-yl)hexane-1,6-diamine, since the melting points of the feed are partially significantly lower (i.e. room temperature or even below for aqueous disrupted N,N'-bis(2,2,6,6-tetramethylpiperidin-4-yl)hexane-1,6-diamine feed), so that clogging of the tube reactor may be avoided and a simple and safe hydrogenation process can be conducted.

In the following, specific embodiments of the presently claimed invention are described:

1. A process for preparing N,N'-bis(2,2,6,6-tetramethylpiperidin-4-yl)hexane-1,6-diamine, wherein the process comprising:
   i. iminating 2,2,6,6-tetramethylpiperidin-4-one with 1,6-hexamethylenediamine to obtain a first mixture comprising N,N'-(hexane-1,6-diyl)bis(2,2,6,6-tetramethylpiperidin-4-imine);
   ii. hydrogenating N,N'-(hexane-1,6-diyl)bis(2,2,6,6-tetramethylpiperidin-4-imine) of the first mixture to obtain a hydrogenated second mixture comprising 50 to 99.5 wt % of N,N'-bis(2,2,6,6-tetramethylpiperidin-4-yl)hexane-1,6-diamine; and
   iii. continuous hydrogenating of the second mixture in a fixed bed reactor to obtain N,N'-bis(2,2,6,6-tetramethylpiperidin-4-yl)hexane-1,6-diamine.
2. The process according to embodiment 1, wherein the first mixture prepared in the step (i) comprises water content in the range of 3 to 7 wt %.
3. The process according to embodiment 1 or 2, further comprising the step of removal of water from the first mixture to have water content less than 2 wt %.
4. The process according to any one of embodiments 1 to 3, further comprising the step of removal of water from the first mixture to have water content less than 1 wt %.
5. The process according to any one of embodiments 1 to 4, further comprising the step of removal of water from the second mixture to have water content less than 2 wt %.
6. The process according to any one of embodiments 1 to 5, further comprising the step of removal of water from the second mixture to have water content less than 1 wt %.
7. The process according to any one of embodiments 1 to 6, wherein the hydrogenation in the step (ii) is performed using batch technology.
8. The process according to any one of embodiments 1 to 7, wherein in the step (ii) the second mixture comprises 65 to 95 wt % of N,N'-bis(2,2,6,6-tetramethylpiperidin-4-yl)hexane-1,6-diamine.

9. The process according to any one of embodiments 1 to 8, wherein the hydrogenation in the step (ii) is catalyzed using at least one first transition metal.
10. The process according to embodiment 9, wherein the first transition metal is selected from copper, nickel, cobalt, ruthenium, platinum, and palladium.
11. The process according to embodiment 8 or 10, wherein the first transition metal is platinum.
12. The process according to any one of embodiments 1 to 6, wherein the continuous hydrogenation of the step (iii) is catalyzed using at least one second transition metal.
13. The process according to embodiment 12, wherein the second transition metal is selected from copper, nickel, cobalt, ruthenium, platinum, and palladium.
14. The process according to embodiment 12 or 13, wherein the transition metal is palladium.
15. The process according to any one of embodiments 1 to 14, wherein the pressure of hydrogen in the hydrogenation step (ii) and the step (iii) is in the range of 1 to 200 bar.
16. The process according to any one of embodiments 1 to 15, wherein the pressure of hydrogen in the hydrogenation step (ii) and the step (iii) is in the range of 5 to 100 bar.
17. The process according to any one of embodiments 1 to 16, wherein a pressure of hydrogen in the hydrogenation step (ii) and the step (iii) is in the range of 5 to 35 bar.
18. The process according to any one of embodiments 1 to 17, wherein a temperature of the step (i) to the step (iii) is in the range of 60 to 200° C.
19. The process according to any one of embodiments 1 to 18, wherein a temperature of the step (i) to the step (iii) is in the range of 80 to 180° C.
20. The process according to any one of embodiments 1 to 19, wherein N,N'-bis(2,2,6,6-tetramethylpiperidin-4-yl)hexane-1,6-diamine obtained in step (iii) has APHA value in the range of 90 to 400.
21. The process according to any one of embodiments 1 to 20, wherein the molar ratio of 1,6-hexamethylenediamine to 2,2,6,6-tetramethylpiperidin-4-one is in the range of 0.1:5 to 5:0.1.
22. The process according to any one of embodiments 1 to 21, wherein the molar ratio of 1,6-hexamethylenediamine to 2,2,6,6-tetramethylpiperidin-4-one is in the range of 1:5 to 5:1.
23. The process according to any one of embodiments 1 to 22, wherein the molar ratio of 1,6-hexamethylenediamine to 2,2,6,6-tetramethylpiperidin-4-one is in the range of 1:2 to 2:1.
24. The process according to any one of embodiments 1 to 23, wherein the molar ratio of 1,6-hexamethylenediamine to 2,2,6,6-tetramethylpiperidin-4-one is in the range of 1:1.98.
25. The process according to any one of embodiments 1 to 24, wherein the molar ratio of hydrogen to N,N'-bis (2,2,6,6-tetramethylpiperidin-4-yl)hexane-1,6-diamine in step (iii) is in the range of 0.5:0.1 to 40:5.
26. The process according to any one of embodiments 1 to 25, wherein the molar ratio of hydrogen to N,N'-bis (2,2,6,6-tetramethylpiperidin-4-yl)hexane-1,6-diamine in step (iii) is in the range of 1:1 to 40:1.
27. The process according to any one of embodiments 1 to 26, wherein the molar ratio of hydrogen to N,N'-bis (2,2,6,6-tetramethylpiperidin-4-yl)hexane-1,6-diamine in step (iii) is in the range of 1.5:1 to 35:1.
28. Use of N,N'-bis(2,2,6,6-tetramethylpiperidin-4-yl) hexane-1,6-diamine obtained by the process according to any one of embodiments 1 to 27, to prepare poly [[6-[(1,1,3,3-tetramethylbutyl)amino]-s-triazine-2,4-diyl]-[(2,2,6,6-tetramethyl-4-piperidyl)imino]-hexamethylene-[(2,2,6,6-tetramethyl-4-piperidyl)imino], reaction material of 1,6-hexanediamine, N,N'-bis (2,2,6,6-tetramethyl-4-piperidine-yl),2,4,6-trichloro-1, 3,5-triazine,N-butyl-1-butylamine, and N-butyl-2,2,6,6-tetramethyl-4-piperidineamine, N,N'-bis(2,2,6,6-tetramethyl-4-piperidyl)-N,N'-diformylhexamethylenediamine, and 1,6-Hexanediamine, N,N'-bis(2,2,6,6-tetramethyl-4-piperidinyl)-, polymer with 2,4-dichloro-6-(4-morpholinyl)-1,3,5-triazine.

The following examples illustrate the invention in greater detail. All percentages and parts are by weight, unless stated otherwise.

EXAMPLES

Abbreviation 2,2,6,6-tetramethylpiperidin-4-one is abbreviated as 'TAA';

N,N'-(hexane-1,6-diyl)bis(2,2,6,6-tetramethylpiperidin-4-imine) is abbreviated as 'HMBTAD Diimine';

N,N'-bis(2,2,6,6-tetramethylpiperidin-4-yl)hexane-1,6-diamine is abbreviated as 'HMBTAD Amine or HMBTAD';

N-(2,2,6,6-tetramethylpiperidin-4-yl)hexane-1,6-diamine is abbreviated as 'HMTAD';

N-isopropyl-N'-(2,2,6,6-tetramethylpiperidin-4-yl) hexane-1,6-diamine is abbreviated as 'IPHMTAD;

1,6-hexamethylenediamine is abbreviated as 'HMDA'; and

LHSV is abbreviated as liquid hour space time velocity and given in $kg_{Feed}/L_{cat}$*h.

Analytical Methods

Selectivities were determined as GC-area-% and confirmed via MS, as well taken from $^{1}H$- or $^{13}C$-NMR Analysis.

Example 1: Preparation of N,N'-bis(2,2,6,6-tetramethylpiperidin-4-yl)hexane-1,6-diamine (HMBTAD) Using Process of the Present Invention

Step (i) and (ii): Ketimine Formation and Disrupted Batch Hydrogenation

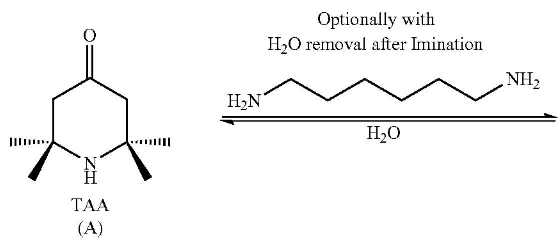

TAA
(A)

-continued

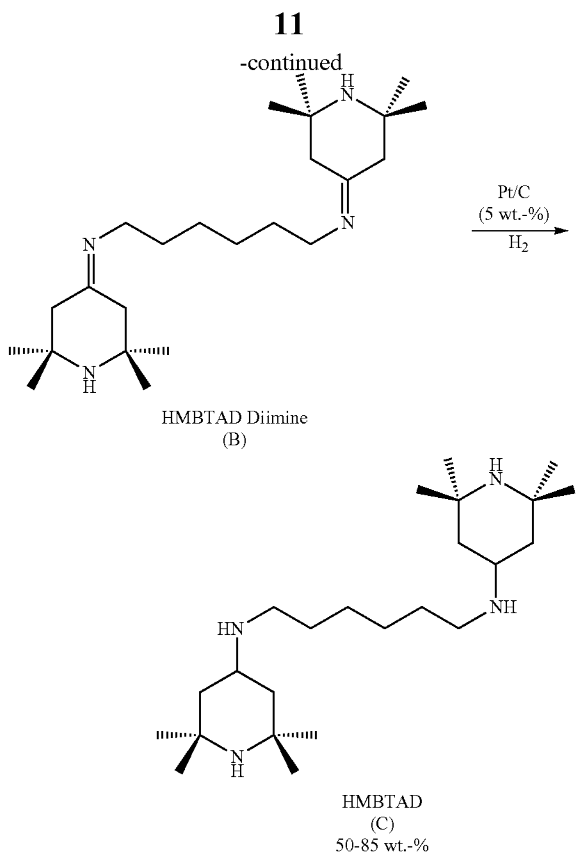

HMBTAD Diimine
(B)

HMBTAD
(C)
50-85 wt.-%

1,6-Hexanediamine (157 g, 1.35 mol, 1.0 equiv.) was added within 10 min to stirred 2,2,6,6-tetramethyl-4-piperidone (423 g, 2.68 mol, 1.98 equiv.) at 60° C. The solution was then heated to 80° C. at which temperature the water of reaction (between 55-75 wt.-%) was removed at reduced pressure (50 mbar). The ketimine solution was then transferred into an autoclave batch reactor and Pt/C catalyst (1.1 g) was added. The hydrogenation was carried out at 80° C. and ramped up to 105° C., with a hydrogen ramp from 5 to 30 bar maximum pressure. The reaction time was kept between 1 and 6 hours until 65 to 99.5% conversion was reached, monitored by GC or $^1$H-NMR or the consumption of hydrogen. The catalyst was then separated from the product by hot filtration.

Analytical Analysis:

$^1$H-NMR (500 MHz, $CDCl_3$): δ=3.31 (t, J=6 Hz, 2H), 2.77-2.74 (m, 1H), 2.63-2.57 (m, 4H), 2.28-2.18 (m, 6H), 1.83-1.80 ($m_c$, 2H), 1.75-1.01 (m, 28H), 0.87 ($m_c$, 3H) ppm.

$^{13}$C-NMR (125 MHz, $CDCl_3$): δ=169.9, 54.0, 53.9, 51.8, 50.9, 50.7, 49.9, 46.7, 46.2, 41.7, 35.1, 31.7, 31.5, 31.0, 30.5, 28.6, 27.6, 27.4 ppm GC-Analysis (30 m×0.32 mm×1.5 μm RTX5 Amine column; injection temperature at 120° C. then heated with 10° C./min to 280° C. and kept 44 min at this temperature): Rt=7.20 (HMDA), 7.75 (TAA), 16.65 (HMTAD), 18.27 (IPHMTAD) and 35.06 (HMBTAD) min, confirmed via MS.

Preparation of Anhydrous HMBTAD Feed for Post Hydrogenation

A dark yellow material from above mentioned disrupted batch hydrogenation (Step (i) and (ii)) containing a HMBTAD amine in an amount of 60%, was removed from water and light boilers via distillation (100×3 cm Sulzer DX column with 30 theoretical stages) at 60-70° C., ramping pressure from 100 mbar to 12 mbar. Between 3-20 wt.-% of the mass of the starting material was removed containing water, acetone and traces of TAA, and leaving a pale-yellow residue which was used for further reaction.

Step (iii): Post Hydrogenation of the Disrupted Batch with Aqueous and Anhydrous HMBTAD Feed The post hydrogenation was conducted with different HMBTAD amine feeds and different transition-metal catalysts (fixed bed on a solid support) at different pressures and within a specific temperature range.

Step (iiia): Post Hydrogenation with Aqueous HMBTAD Feed and a [Pd] Catalyst

In a monoliner reactor equipped with an inner thermowell, aqueous HMBTAD amine feed (containing 12 wt.-% HMBTAD amine and 5 wt.-% $H_2O$) was continuously led together with hydrogen gas, over a fixed bed catalyst (114 g) on a solid support (e.g. $Al_2O_3$ or others) consisting of Pd (typically 0.1-1.0, here 0.7%) as the active metal. The pressure was at 30 bar, the temperatures varied between 100-180° C., preferably at 150° C. The HMBTAD amine feed was fed into the reactor with LHSV between 0.5-1.0 $kg_{Feed}/L_{cat}$*h. The crude product was collected after the reactor and obtained as a neat liquid. Remaining volatiles in the mix were subsequently removed at 180° C. and 10 mbar to give a pale-yellow liquid which crystallized upon standing at room temperature to an off-white solid product and an APHA value of 262 (DIN-ISO 6271). The selectivities of HMBTAD and side components in the product mix was analyzed via GC and given in area-% and is furthermore dependent from the conditions. The amount of HMBTAD and side components in the product mix are given in Tables 1, 2, 3, and 4.

TABLE 1

| $LHSV_{HMBTAD}$ [kg/L * h] | Rx.-Temp. [° C.] | Molar Ratio ($H_2$:HMBTAD) | $p_{H2}$ [bar] | TAA [%] | HMTAD [%] | IPHMTAD [%] | HMBTAD [%] |
|---|---|---|---|---|---|---|---|
| 0.5 | 150 | 35:1 | 30 | 0.0 | 0.0 | 8.7 | 86.0 |
| 0.5 | 150 | 20:1 | 30 | 0.1 | 0.0 | 8.8 | 85.2 |
| 0.7 | 150 | 20:1 | 30 | 0.1 | 0.0 | 8.2 | 87.1 |
| 1.0 | 150 | 20:1 | 30 | 0.1 | 0.0 | 8.4 | 87.7 |

TABLE 2

| $LHSV_{HMBTAD}$ [kg/L * h] | Rx.- Temp. [° C.] | Molar Ratio ($H_2$:HMBTAD) | $p_{H2}$ [bar] | TAA [%] | HMTAD [%] | IPHMTAD [%] | HMBTAD [%] |
|---|---|---|---|---|---|---|---|
| 1.0 | 180 | 20:1 | 30 | 0.1 | 0.0 | 7.3 | 81.2 |
| 1.0 | 150 | 20:1 | 30 | 0.1 | 0.0 | 8.4 | 87.7 |
| 1.0 | 130 | 20:1 | 30 | 0.1 | 0.0 | 8.1 | 88.8 |
| 1.0 | 115 | 20:1 | 30 | 0.1 | 0.1 | 8.3 | 88.4 |
| 1.0 | 100 | 20:1 | 30 | 0.1 | 0.1 | 7.1 | 86.1 |

TABLE 3

| $LHSV_{HMBTAD}$ [kg/L * h] | Rx.- Temp. [° C.] | Molar Ratio ($H_2$:HMBTAD) | $p_{H2}$ [bar] | TAA [%] | HMTAD [%] | IPHMTAD [%] | HMBTAD [%] |
|---|---|---|---|---|---|---|---|
| 0.7 | 150 | 35:1 | 30 | 0.0 | 0.0 | 7.7 | 88.4 |
| 0.7 | 150 | 20:1 | 30 | 0.1 | 0.0 | 8.2 | 87.1 |
| 0.7 | 150 | 1.5:1 | 30 | 0.1 | 0.0 | 9.2 | 82.0 |

TABLE 4

| $LHSV_{HMBTAD}$ [kg/L * h] | Rx.- Temp. [° C.] | Molar Ratio ($H_2$:HMBTAD) | $p_{H2}$ [bar] | TAA [%] | HMTAD [%] | IPHMTAD [%] | HMBTAD [%] |
|---|---|---|---|---|---|---|---|
| 1.0 | 100 | 1.5:1 | 30 | 0.2 | 0.1 | 6.9 | 89.3 |
| 1.0 | 115 | 1.5:1 | 30 | 0.1 | 0.1 | 8.2 | 88.9 |
| 1.0 | 130 | 1.5:1 | 30 | 0.3 | 0.1 | 8.6 | 87.1 |
| 1.0 | 150 | 1.5:1 | 30 | 0.1 | 0.0 | 8.0 | 88.2 |
| 1.0 | 180 | 1.5:1 | 30 | 0.1 | 0.0 | 7.7 | 83.0 |

Step (iiib): Post Hydrogenation with Anhydrous HMBTAD Food and a [Pd] Catalyst

In a monoliner reactor equipped with an inner thermowell, anhydrous HMBTAD amine feed (containing 68 wt.-% HMBTAD amine and <0.5 wt.-% $H_2O$) was continuously led together with hydrogen gas, over a fixed bed catalyst (115 g) on a solid support (e.g. $Al_2O_3$ or others) consisting of Pd (typically 0.1-1.0, here 0.7%) as the active metal. The pressure was in the range of 10-80 bar, preferably at 30 bar, the temperatures varied between 100-180° C., preferably at 130° C. The HMBTAD amine feed was fed into the reactor with LHSV between 1.0-1.6 $kg_{Feed}/L_{cat}$*h. The crude product was collected after the reactor and obtained as a neat liquid. Remaining volatiles in the mix were subsequently removed at 180° C. and 10 mbar to give a pale-yellow liquid which crystallized upon standing at room temperature to an off-white solid product with an APHA value of 126 (DIN-ISO 6271). The selectivities of HMBTAD and side components in the product mix was analyzed via GC and given in area-% and is furthermore dependent from the conditions. The amount of HMBTAD and side components in the product mix are given in Tables 5, 6, 7, and 8.

TABLE 5

| $LHSV_{HMBTAD}$ [kg/L * h] | Rx.- Temp. [° C.] | Molar Ratio ($H_2$:HMBTAD) | $p_{H2}$ [bar] | TAA [%] | HMTAD [%] | IPHMTAD [%] | HMBTAD [%] |
|---|---|---|---|---|---|---|---|
| 1.0 | 130 | 20:1 | 30 | 0.1 | 0.2 | 4.5 | 93.0 |
| 1.0 | 130 | 1.5:1 | 30 | 0.1 | 0.2 | 4.1 | 93.6 |
| 1.2 | 130 | 1.5:1 | 30 | 0.1 | 0.4 | 4.0 | 93.5 |
| 1.4 | 130 | 1.5:1 | 30 | 0.1 | 0.4 | 4.0 | 93.5 |
| 1.6 | 130 | 1.5:1 | 30 | 0.1 | 0.4 | 3.8 | 94.0 |

TABLE 6

| $LHSV_{HMBTAD}$ [kg/L * h] | Rx.- Temp. [° C.] | Molar Ratio ($H_2$:HMBTAD) | $p_{H2}$ [bar] | TAA [%] | HMTAD [%] | IPHMTAD [%] | HMBTAD [%] |
|---|---|---|---|---|---|---|---|
| 1.4 | 100 | 20:1 | 30 | 0.1 | 0.5 | 3.7 | 89.8 |
| 1.4 | 115 | 20:1 | 30 | 0.1 | 0.7 | 3.1 | 92.7 |
| 1.4 | 130 | 20:1 | 30 | 0.1 | 0.5 | 3.4 | 93.7 |

TABLE 6-continued

| $LHSV_{HMBTAD}$ [kg/L * h] | Rx.-Temp. [° C.] | Molar Ratio ($H_2$:HMBTAD) | $p_{H2}$ [bar] | TAA [%] | HMTAD [%] | IPHMTAD [%] | HMBTAD [%] |
|---|---|---|---|---|---|---|---|
| 1.4 | 150 | 20:1 | 30 | 0.1 | 0.4 | 4.5 | 91.9 |
| 1.4 | 180 | 20:1 | 30 | 0.0 | 0.1 | 9.0 | 80.7 |

TABLE 7

| $LHSV_{HMBTAD}$ [kg/L * h] | Rx.-Temp. [° C.] | Molar Ratio ($H_2$:HMBTAD) | $p_{H2}$ [bar] | TAA [%] | HMTAD [%] | IPHMTAD [%] | HMBTAD [%] |
|---|---|---|---|---|---|---|---|
| 1.4 | 100 | 1.5:1 | 30 | 0.1 | 0.5 | 3.3 | 90.1 |
| 1.4 | 115 | 1.5:1 | 30 | 0.1 | 0.4 | 3.9 | 92.8 |
| 1.4 | 130 | 1.5:1 | 30 | 0.1 | 0.4 | 4.0 | 93.5 |
| 1.4 | 150 | 1.5:1 | 30 | 0.0 | 0.4 | 4.6 | 92.1 |
| 1.4 | 180 | 1.5:1 | 30 | 0.0 | 0.1 | 8.2 | 82.2 |

TABLE 8

| $LHSV_{HMBTAD}$ [kg/L * h] | Rx.-Temp. [° C.] | Molar Ratio ($H_2$:HMBTAD) | $p_{H2}$ [bar] | TAA [%] | HMTAD [%] | IPHMTAD [%] | HMBTAD [%] |
|---|---|---|---|---|---|---|---|
| 1.4 | 130 | 1.5:1 | 10 | 0.1 | 0.5 | 3.5 | 93.7 |
| 1.4 | 130 | 1.5:1 | 30 | 0.1 | 0.4 | 4.0 | 93.5 |
| 1.4 | 130 | 1.5:1 | 80 | 0.1 | 0.4 | 3.5 | 93.9 |

Step (iiic): Post Hydrogenation with Anhydrous HMBTAD Feed and with Other Transition Metal Catalysts In a tubular reactor equipped with an inner thermowell, anhydrous HMBTAD amine feed (containing 68 wt.-% HMBTAD amine and <0.5 wt.-% $H_2O$) was continuously led together with hydrogen gas, over a fixed bed catalyst (500 mL) on a solid support ($Al_2O_3$) consisting of Co, Ni and Cu as the active metal. The pressure was at 30 bar, the temperatures were varied between 130 and 150° C. The HMBTAD Amine feed was fed into the reactor with a LHSV of 0.55 and 0.8 $kg_{Feed}/L_{cat}$*h. The crude product was collected after the reactor and obtained as a neat liquid. Remaining volatiles in the mix were subsequently removed at 180° C. and 10 mbar to give a pale-yellow liquid which crystallized upon standing at room temperature to an off-white solid product with APHA values of 181 and 379, respectively (DIN-ISO 6271). The selectivities of HMBTAD and side components in the product mix was analyzed via GC and given in area-% and is furthermore dependent from the conditions. The amount of HMBTAD and side components in the product mix, wherein HMBTAD amine feed were passed over the fixed bed catalyst containing [Ni] and [Co] as active metal species on an $Al_2O_3$ support, are given in Table 9.

TABLE 9

| $LHSV_{HMBTAD}$ [kg/L * h] | Rx.-Temp. [° C.] | Molar Ratio ($H_2$:HMBTAD) | $p_{H2}$ [bar] | TAA [%] | HMTAD [%] | IPHMTAD [%] | HMBTAD [%] |
|---|---|---|---|---|---|---|---|
| 0.55 | 130 | 20:1 | 30 | 0.1 | 0.4 | 3.5 | 94.1 |
| 0.55 | 150 | 20:1 | 30 | 0.1 | 0.3 | 3.4 | 93.2 |
| 0.8 | 130 | 20:1 | 30 | 0.1 | 0.6 | 3.4 | 93.5 |
| 0.8 | 150 | 20:1 | 30 | 0.1 | 0.3 | 3.4 | 93.0 |

TABLE 10

| Storage Time at 60° C. [days] | Color index [APHA] [Co] [Cu] and [Ni] Catalyst on $Al_2O_3$ Support |
|---|---|
| 0 (at RT) | 379 |
| 1 | 408 |
| 2 | 443 |
| 5 | 501 |

The amount of HMBTAD and side components in the product mix, wherein HMBTAD amine feed were passed over the fixed bed catalyst containing [Cu] as active metal species on an $Al_2O_3$ support, are given in Table 11.

TABLE 11

| LHSV$_{HMBTAD}$ [kg/L * h] | Rx.- Temp. [° C.] | Molar Ratio ($H_2$:HMBTAD) | $p_{H2}$ [bar] | TAA [%] | HMTAD [%] | IPHMTAD [%] | HMBTAD [%] |
|---|---|---|---|---|---|---|---|
| 0.55 | 130 | 20:1 | 30 | 0.2 | 0.6 | 3.2 | 93.5 |
| 0.55 | 150 | 20:1 | 30 | 0.1 | 0.3 | 3.3 | 93.6 |
| 0.8 | 130 | 20:1 | 30 | 0.2 | 0.5 | 3.3 | 94.3 |
| 0.8 | 150 | 20:1 | 30 | 0.1 | 0.4 | 3.3 | 93.8 |

TABLE 12

| Storage Time at 60° C [days] | Color index [APHA] [Cu] Catalyst on $Al_2O_3$ Support |
|---|---|
| 0 (at RT) | 181 |
| 1 | 188 |
| 2 | 209 |
| 5 | 228 |
| 6 | 243 |
| 7 | 231 |

Step (iiid): Post Hydrogenation of Distilled HMBTAD with a [Pd] Catalyst and Prepared by EP0508940

In a tubular reactor equipped with an inner thermowell, pre-distilled HMBTAD amine prepared by EP0508940 (containing 91 wt.-% HMBTAD Amine and <0.1 wt.-% $H_2O$) was continuously led together with 150 NL/h (molar ratio $H_2$ to HMBTAD of 17:1) hydrogen gas, over a fixed bed catalyst (500 mL) on a solid support ($Al_2O_3$) consisting of Pd (0.3%) and Ag (0.1%) as the active metals. The pressure was at 30 bar, the temperature between 115° C. The HMBTAD amine feed was fed into the reactor with a LHSV of 0.3-0.4 $kg_{Feed}/L_{cat}$*h. The crude product was collected after the reactor and obtained as a neat colorless liquid which crystallized upon standing at room temperature to an off-white solid product with an APHA value of 153 (DIN-ISO 6271) containing >93 GC-area-% HMBTAD, 1 GC-area-% HMTAD and 4 GC-area-% IPHMTAD.

Comparative Example 1: Preparation of HMBTAD by a Fully Continuous Hydrogenation Process Starting from TAA and HMDA (According to EP0857719 and U.S. Pat. No. 5,945,536) and Subsequent Distillation As described in EP0857719 and U.S. Pat. No. 5,945,536, TAA and HMDA (as a 50 wt.-% solution in THF) were continuously led together in a molar ratio of 2:1 with 100 NL/h hydrogen gas in a tubular reactor equipped with an inner thermowell and over a fixed bed catalyst (500 mL) on a solid support ($Al_2O_3$) consisting of Pd (0.7%) as the active metal. The pressure was at 180 bar, the temperature at 115° C. The HMBTAD amine feed was fed into the reactor with a LHSV of 0.3-0.4 $kg_{Feed}/L_{cat}$*h. The crude product was collected after the reactor and obtained as dark orange liquid which crystallized upon standing at room temperature to an orange solid product with an APHA value of 703 (DIN-ISO 6271) containing 87.8 GC-area-% HMBTAD, 3.2 GC-area-% HMTAD and 0.4 GC-area-% IPHMTAD. The crude product was purified via fractioned distillation (100×4.2 cm Sulzer DX column with 25-30 theoretical stages) starting at 90° C. for water removal and increased to 240° C. temperature while ramping pressure from 100 mbar to 6 mbar. The target molecule HMBTAD amine (b.p. 225° C. at 6 mbar) was obtained in >99% purity in 84% yield with an APHA value of 190 (DIN-ISO 6271).

Comparative Example 2: Preparation of HMBTAD by Batch Hydrogenation (EP0508940) without Distillation According to EP0508940, 1,6-Hexanediamine (157 g, 1.35 mol, 1.0 equiv.) was added within 10 min to stirred 2,2,6,6-tetramethyl-4-piperidone (423 g, 2.68 mol, 1.98 equiv.) at 60° C. The solution was then heated to 80° C. at which temperature the water of reaction (between 55-75 wt.-%) was removed at reduced pressure (50 mbar). The ketimine solution was then transferred into an autoclave batch reactor and Pt/C catalyst (1.1 g) was added. The hydrogenation was carried out at 80° C. and ramped up to 105° C., with a hydrogen ramp from 5 to 30 bar maximum pressure. The reaction time was kept for 12 hours until 99.5% conversion was reached, monitored by GC or $^1$H-NMR or the consumption of hydrogen. The catalyst was then separated from the product by hot filtration. Remaining volatiles in the mix were subsequently removed at 180° C. and 10 mbar to give a pale-yellow liquid which crystallized upon standing at room temperature to an off-white solid product with an APHA value of 220 (DIN-ISO 6271).

Quality and Color Assay Before and After Storage of HMBTAD at Elevated Temperatures According to DIN-ISO 6271, the color index of the products was measured neat and not dissolved by a Hach Lico 620 apparatus in a cuvette. The products were stored at 60° C. under nitrogen for several days and the color index was detected within specific time periods. The results are given in the following Table 13 in their APHA values:

TABLE 13

| Storage Time at 60° C. [days] | Color index [APHA] | | | |
|---|---|---|---|---|
| | HMBTAD [Comparative example 1] (EP0857719; Continuous process) | HMBTAD [Comparative example 2] (EP0508940; Batch process) | HMBTAD [present invention; step (iiia)] (from post-hydrogenating aqueous free feed, <0.5% $H_2O$) | HMBTAD [present invention; (step iiib)] (from post-hydrogenating aqueous feed, 5% $H_2O$) |
| 0 (at RT) | 190 | 220 | 126 | 262 |
| 4 | n.d. | 407 | 133 | 331 |
| 7 | n.d. | 514 | 142 | 386 |
| 11 | n.d. | 704 | 164 | 442 |
| 14 | n.d. | 818 | 186 | 479 |
| 18 | n.d. | 942 | 193 | 526 |
| 20 | n.d. | >1000 | 221 | 563 |

From Table 13, it is evident that the HMBTAD prepared in accordance with the batch process of EP0508940 is not stable for longer periods of time and tends to darken quite fast within only 20 days, whereas HMBTAD prepared in accordance with the process of the present invention is obtained with equal or significantly better color indices and only slight deterioration over time. Even over a long period of time at elevated temperatures HMBTAD of the present application is very stable in its quality when starting with aqueous feed, and with non-aqueous feed.

Example 2: Preparation of poly[[6-[(1,1,3,3-tetramethylbutyl)amino]-s-triazine-2,4-diyl]-[(2,2,6,6-tetramethyl-4-piperidyl)imino]-hexamethylene-[(2,2,6,6-tetramethyl-4-piperidyl)imino] and Assay of the Transmittance (T %)

In a 1-liter glass reactor, HMBTAD amine (186 g, 0.47 mol, 1.1 equiv.) was molten at 80° C. NaOH (30% in $H_2O$, 67 g, 0.50 mol, 1.15 equiv.) was added together with 30 g of water. Through a dropping funnel 2,4-dichloro-6-(1,1,3,3-tetramethylbutylamino)-1,3,5-triazine (282 g, 0.43 mol, 1.0 equiv.) which was prepared via CN108623566 or U.S. Pat. No. 6,407,254 and dissolved in xylene, was charged within 1 hour maintaining the temperature at 90° C. The reaction mixture was stirred for 30 minutes at 95° C. After complete reaction, the reaction was quenched by separating the aqueous phase. The xylenic solution was then transferred into a 1-liter autoclave and treated with NaOH (30% in $H_2O$, 69 g, 0.49 mol, 1.13 equiv.) and heated up to 180° C. at 9 bar pressure and kept at this temperature for 4 h. The slurry was then cooled to 85° C. within 1 hour. The reaction mixture was next transferred into a glass line reactor, diluted with xylene (134 g) and washed with aq. $NaHCO_3$ solution (10% in $H_2O$, 70 g). Stirring the mixture 0.5 h at 95° C. the aq. phase was separated, and the organic phase was filtered at 90° C. The solvent was removed under reduced pressure at 200° C. to obtain a white or pale-yellow solid product. Transmittance values were detected as 10 wt.-% toluenic solution at 425 nm and given in the following Table 14:

TABLE 14

| Source | Delta T % |
|---|---|
| HMBTAD (prepared by EP0508940) [Comparative example 2] | Reference |
| HMBTAD by Post Hydrogenation of aqueous Feed Step (iiia) | +2 |
| HMBTAD By Post Hydrogenation of aqueous-free Feed Step (iiib) | +3.3 |

Example 3: Preparation of N,N'-bis(2,2,6,6-tetramethyl-4-piperidyl)-N,N'-diformylhexamethylenediamine and Assay of the Color index (APHA)

N,N'-bis(2,2,6,6-tetramethyl-4-piperidyl)-N,N'-diformylhexamethylenediamine was prepared according to US20100160637 (Example 6). 40 ml of formamide and 170 g of N,N'-bis(2,2,6,6-tetramethylpiperidin-4-yl)hexane-1,6-diamine were added to 60 ml of xylene. 20 ml of acetic acid were added, and the mixture was heated to reflux temperature under an inert gas atmosphere. After a reaction time of 10 hours, the reaction mixture was cooled to approximately 90° C. to 95° C., and 40 ml of water were allowed to run in with stirring. Then, with further stirring, sufficient aqueous sodium hydroxide solution to quench the excess formamide was added. The reaction mixture was refluxed again and xylene was distilled off azeotropically. Then, the mixture was cooled to approximately 60° C., water was added, and the resulting solid product residues separated off. The product residue was thoroughly washed with water and then dried. Drying gives the product in a specific yield, chemical purity and color index, dependent of the quality of the starting material HMBTAD as shown by table 15. Specification for the color index was a maximum of 200 APHA.

TABLE 15

| Source | Yield [%] | Purity [%] | Color index [APHA] |
|---|---|---|---|
| HMBTAD (prepared by EP0857719) [Comparative example 1] | 96.7 | 99.7 | 17 |
| HMBTAD (prepared by EP0508940) [Comparative example 2] | 90.1 | 97.1 | 267 |
| HMBTAD by Post Hydrogenation of aqueous Feed Step (iiia) | 88.0 | 98.9 | 191 |

TABLE 15-continued

| Source | Yield [%] | Purity [%] | Color index [APHA] |
|---|---|---|---|
| HMBTAD by Post Hydrogenation of aqueous-free Feed Step (iiib) | 90.6 | 98.8 | 49 |

Example 4: Preparation of Reaction Material of 1,6-hexanediamine, N,N'-bis (2,2,6,6-tetramethyl-4-piperidine-yl),2,4,6-trichloro-1, 3,5-triazine,N-butyl-1-butylamine, and N-butyl-2,2,6,6-tetramethyl-4-piperidineamine and Assay of Transmittance (T %)

According to a procedure described in EP0782994 (Example 10), a xylenic solution of N-butyl-4,6-dichloro-N-(2,2,6,6-tetramethylpiperidin-4-yl)-1,3,5-triazin-2-amine (387 g, 0.32 mol, which was prepared accordingly to previous U.S. Pat. No. 4,086,204 or CN107033127 and starting from commercial available cyanuric chloride with a purity of >99%) was stirred at 50° C. in 1 liter glass reactor. A mixture of molten N,N'-bis[2,2,6,6-tetramethyl-4-piperidyl]hexamethylendiamine (HMBTAD) (66.8 g, 0.17 mol) and water (45 g) was slowly added using a dropping funnel. Once 20% of the mixture had been added, a solution of NaOH 30% (45.6 g, 0.34 mol) was charged using another dropping funnel. The two dropwise additions finished at the same time. The overall procedure takes places in 2 hours, in which the temperature was increased up to 80° C. After this, the reaction mixture was stirred for additional 30 minutes at 85° C. Then the stirrer was stopped, and the aqueous phase was separated. The xylenic solution concentrated at the rotavapor (80° C. 80 mbar) to reach a concentration around 50% (344 g, 0.17 mol). Then, the mixture was transferred into 1 liter autoclave together with HMBTAD (126 g, 0.32 mol), NaOH 30% solution (46 g, 0.34 mol) and water (18 g). Reaction mass was heated up to 175° C. and 9 bar pressure and kept at this temperature for 4 hours, then cooled down to 85° C. in 1 hour. Reaction mixture was transferred into a glass reactor, diluted with xylene (152 g) and 10% $NaHCO_3$ solution (63 g) was added for washing. After 15 minutes of stirring at 95° C. the mixture was cooled to 85° C. and the aqueous phase was separated. The reaction proceeds accordingly to standard procedure in the following steps. The values of Transmittance were detected on 10% toluenic solution at 425 nm and given in the following Table 16:

TABLE 16

| Source | Delta T % |
|---|---|
| HMBTAD (prepared by EP0508940) [Comparative example 2] | Reference |
| HMBTAD by Post Hydrogenation of aqueous-free Feed Step (iiib) | +2.5 |

The invention claimed is:

1. A process for preparing N,N'-bis(2,2,6,6-tetramethylpiperidin-4-yl)hexane-1,6-diamine, wherein the process comprising:
(i) iminating 2,2,6,6-tetramethylpiperidin-4-one with 1,6-hexamethylenediamine to obtain a first mixture comprising N,N'-(hexane-1,6-diyl)bis(2,2,6,6-tetramethylpiperidin-4-imine);
(ii) hydrogenating N,N'-(hexane-1,6-diyl)bis(2,2,6,6-tetramethylpiperidin-4-imine) of the first mixture to obtain a hydrogenated second mixture comprising 50 to 99.5 wt % of N,N'-bis(2,2,6,6-tetramethylpiperidin-4-yl)hexane-1,6-diamine; and
(iii) continuous hydrogenating of the second mixture in a fixed bed reactor to obtain N,N'-bis(2,2,6,6-tetramethylpiperidin-4-yl)hexane-1,6-diamine.

2. The process according to claim 1, wherein the first mixture prepared in the step (i) comprises water content in the range of 3 to 7 wt %.

3. The process according to claim 1, further comprising the step of removal of water from the first mixture to have water content less than 2 wt %.

4. The process according to claim 1, further comprising the step of removal of water from the second mixture to have water content less than 2 wt %.

5. The process according to claim 1, wherein in the step (ii) the second mixture comprises 65 to 95 wt % of N,N'-bis(2,2,6,6-tetramethylpiperidin-4-yl)hexane-1,6-diamine.

6. The process according to claim 1, wherein the hydrogenation in the step (ii) is catalyzed using at least one first transition metal.

7. The process according to claim 6, wherein the first transition metal is selected from copper, nickel, cobalt, ruthenium, platinum, and palladium.

8. The process according to claim 6, wherein the first transition metal is platinum.

9. The process according to claim 1, wherein the continuous hydrogenation of the step (iii) is catalyzed using at least one second transition metal.

10. The process according to claim 9, wherein the second transition metal is selected from copper, nickel, cobalt, ruthenium, platinum, and palladium.

11. The process according to claim 9, wherein the transition metal is palladium.

12. The process according to claim 1, wherein the pressure of hydrogen in the hydrogenation step (ii) and the step (iii) is in the range of 1 to 200 bar.

13. The process according to claim 1, wherein a temperature of the step (i) to the step (iii) is in the range of 60 to 200° C.

14. The process according to claim 1, wherein N,N'-bis (2,2,6,6-tetramethylpiperidin-4-yl)hexane-1,6-diamine obtained in step (iii) has APHA value in the range of 90 to 400.

15. The process according to claim 1, wherein the molar ratio of 1,6-hexamethylenediamine to 2,2,6,6-tetramethylpiperidin-4-one is in the range of 0.1:5 to 5:0.1.

16. The process according to claim 1, wherein the molar ratio of hy-drogen to N,N'-bis(2,2,6,6-tetramethylpiperidin-4-yl)hexane-1,6-diamine in step (iii) is in the range of 0.5:0.1 to 40:5.

* * * * *